US00PP30050P3

(12) United States Plant Patent
Schoone

(10) Patent No.: US PP30,050 P3
(45) Date of Patent: Jan. 1, 2019

(54) ***PHALAENOPSIS* ORCHID PLANT NAMED 'PENNY LOVE'**

(50) Latin Name: *Phalaenopsis hybrida*
Varietal Denomination: Penny Love

(71) Applicant: Floricultura, Heemskerk (NL)

(72) Inventor: René Schoone, Assendelft (NL)

(73) Assignee: FLORICULTURA, Heemskerk (NL)

( * ) Notice: Subject to any disclaimer, the term of this patent is extended or adjusted under 35 U.S.C. 154(b) by 0 days.

(21) Appl. No.: 15/731,131

(22) Filed: Apr. 25, 2017

(65) Prior Publication Data

US 2017/0311519 P1 Oct. 26, 2017

Related U.S. Application Data

(60) Provisional application No. 62/327,850, filed on Apr. 26, 2016.

(30) Foreign Application Priority Data

Apr. 29, 2016 (NL) ..... PBR OPS1335

(51) Int. Cl.
*A01H 5/02* (2018.01)

(52) U.S. Cl.
USPC ..... Plt./311
CPC ..... *A01H 5/02* (2013.01)

(58) Field of Classification Search
USPC ..... Plt./311
CPC ... A01H 5/02; A01H 5/00; A01H 5/08; A01H 6/62
See application file for complete search history.

(56) References Cited

U.S. PATENT DOCUMENTS

PP27,230 P3 * 10/2016 Schoone ..... A01H 5/02 Plt./311

* cited by examiner

*Primary Examiner* — June Hwu
(74) *Attorney, Agent, or Firm* — Foley & Lardner LLP; Sunit Talapatra

(57) ABSTRACT

A new and distinct *Phalaenopsis* plant named 'Penny Love' particularly characterized by flowers which are yellow with red/purple stripes and a red/purple labellum; plants which may be propagated economically and uniformly using tissue culture; plants which produce more than one inflorescence; long and sturdy inflorescences; and relatively short, dark-green foliage.

3 Drawing Sheets

Latin name of the genus and species of the plant claimed: *Phalaenopsis hybrida.*

Variety denomination: 'Penny Love'.

BACKGROUND OF THE INVENTION

The present invention relates to a new and distinct cultivar of *Phalaenopsis* plant, botanically known as *Phalaenopsis* of the Orchidaceae family, and hereinafter referred to by the cultivar name 'Penny Love'.

*Phalaenopsis* comprises a genus of about 55 species of herbaceous perennials many of which, or the hybrids thereof, are suitable for cultivation in the home or greenhouse. *Phalaenopsis* is predominantly epiphytic or rock-dwelling, and is native to tropical Asia, the Malay Archipelago, and Oceania. The species typically has 2-ranked, fleshy, oblong or elliptic leaves affixed to a short central stem (monopodial growth), which vary in size from 5 to 8 inches to over 2 feet. The leaves may be entirely green or mottled with silver grey.

*Phalaenopsis* orchids, often referred to as 'Moth Orchids' in the horticultural trade, are frequently used to furnish cut flowers for the florist trade or sold as flowering potted-plants for home or interiorscape.

*Phalaenopsis* produces upright or pendent lateral racemes, often with many showy flowers which open in succession beginning with the lowermost. The flowers possess three sepals and three petals; the lateral ones being alike. The lowermost petal, called the labellum, is three-lobed and is often more brightly-colored than the other flower segments. Flower colors include various shades of pink, white, yellow and red-brown.

*Phalaenopsis* orchids are typically propagated from seeds. Asexual propagation of *Phalaenopsis* is often done from off-shoots which frequently arise from the lower bracts of the inflorescence. The resulting plants are detached from the mother plant and may be planted in a suitable substrate.

The new *Phalaenopsis* 'Penny Love' is a product of a controlled breeding program conducted by the inventor, René Schoone, in Strengweg, Heemskerk, The Netherlands. The objective of the breeding program was to develop a new *Phalaenopsis* cultivar particularly characterized by its attractive and unique colored flowers, economical propagation via tissue culture, rapid growth, and a plant dimension suitable for packaging and shipping to the market.

The new *Phalaenopsis* 'Penny Love' originated from a cross made by the inventor in 2003 in Strengweg, Heemskerk, The Netherlands. The female or seed parent is the *Phalaenopsis* cultivar designated 'Sunrise Delight', unpatented. The male or pollen parent is the *Phalaenopsis* cultivar designated 'Timothy Christopher', unpatented. The new *Phalaenopsis* 'Penny Love' was discovered and selected by the inventor as a single flowering plant within the progeny of the stated cross in a controlled environment in 2011 in Strengweg, Heemskerk, The Netherlands.

Asexual reproduction of the new *Phalaenopsis* cultivar by tissue culture (mericloning) was first performed in November, 2011 in Cieweg 13, Heemskerk, The Netherlands, and has demonstrated that the combination of characteristics as herein disclosed for the new cultivar are firmly fixed and retained through successive generations of asexual reproduction. The new cultivar asexually reproduces true-to-type.

BRIEF DESCRIPTION OF THE INVENTION

The following traits have been repeatedly observed and are determined to be unique characteristics of 'Penny Love', which in combination distinguish this *Phalaenopsis* as a new and distinct cultivar:

1. flowers which are yellow with red/purple stripes and a red/purple labellum;
2. plant produces more than one inflorescence;
3. plants may be propagated economically and uniformly using tissue culture;
4. inflorescences are long and sturdy; and
5. relatively short, dark-green foliage.

In comparison with the parental cultivars of 'Penny Love', the female parent 'Sunrise Delight' is yellow/orange with red/purple stripes and pink in the labellum, the male parent 'Timothy Christopher' is white with a little yellow in labellum, whereas the flowers of 'Penny Love' are yellow with red/purple stripes and a red/purple labellum.

Presently, the commercial cultivar to which 'Penny Love' can be meaningfully compared is 'Penny Lane', U.S. Plant Pat. No. 27,230. The flowers of 'Penny Lane', U.S. Plant Pat. No. 27,230 are darker yellow and have more red/purple stripes. The color of the midlobe of 'Penny Lane' is RHS 60B, while the color of the midlobe of 'Penny Love' is RHS 71A. The shape differs, because the lateral petals of 'Penny Love' touch the column, white the lateral petals of 'Penny Lane' do not reach the column.

BRIEF DESCRIPTION OF THE PHOTOGRAPHS

The accompanying photographs illustrate the overall appearance of the new *Phalaenopsis* 'Penny Love' showing the colors as true as is reasonably possible with colored reproductions of this type. Colors in the photographs may differ slightly from the color values cited in the detailed botanical description, which accurately describe the color of 'Penny Love'.

DETAILED BOTANICAL DESCRIPTION

Figure 1:
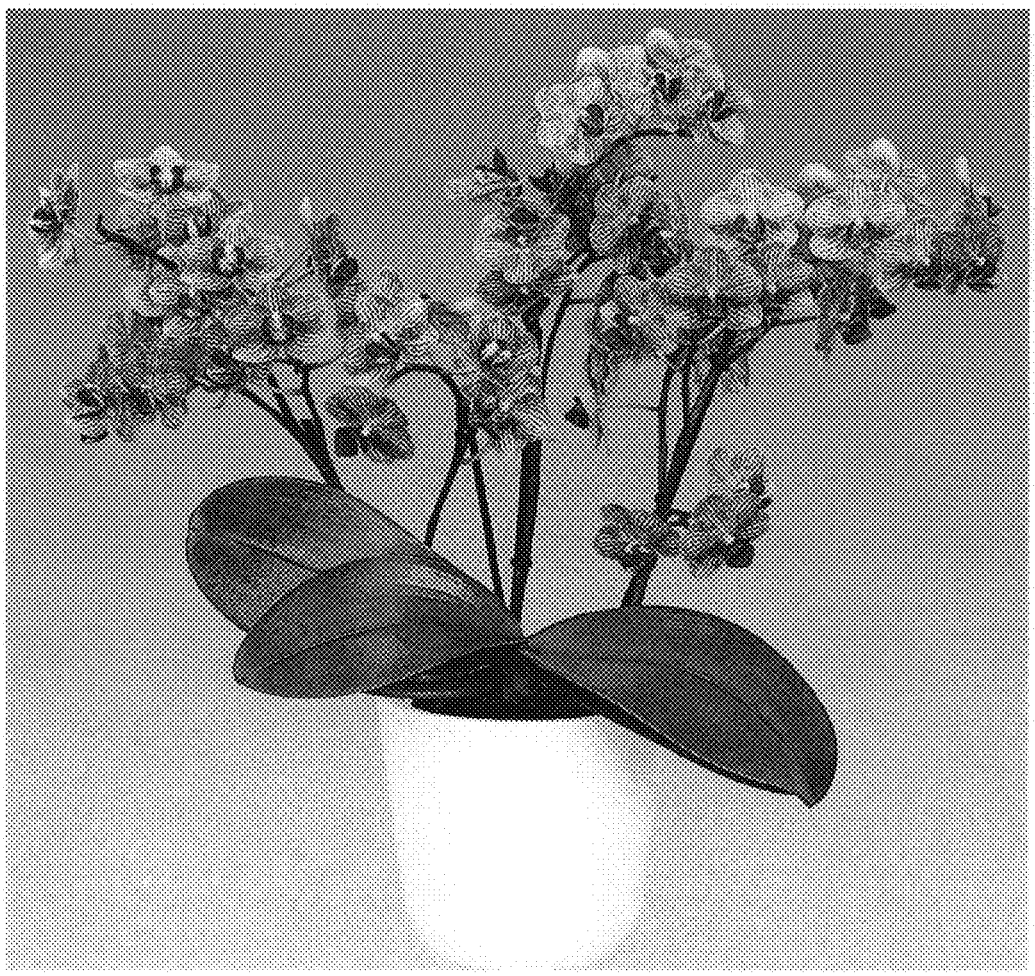
FIG. 1 shows a side view perspective of a typical flowering plant of 'Penny Love' in a 12 cm pot, at 16 months of age.

The new *Phalaenopsis* cultivar 'Penny Love' has not been observed under all possible environmental conditions. The phenotype of the new cultivar may vary with variations in environment such as temperature, light intensity, and day length without any change in the genotype of the plant.

The aforementioned photographs, together with the following observations, measurements and values describe plants of 'Penny Love' as grown in a greenhouse in Strengweg, Heemskerk, The Netherlands, under conditions which closely approximate those generally used in commercial practice. Initially, the ideal temperature to grow plants of 'Penny Love' is 27° C. during the day and at night. Then, during the flowering phase of 'Penny Love', the ideal growing temperature is 20-22° C. during the day and 18° C. at night. Light levels for growing 'Penny Love' are a minimum of 5,000 lux and a maximum of 10,000 lux. A balanced fertilizer with level of 200 ppm N, 87 ppm P, 168 ppm K is applied. Duration of growth of 'Penny Love' from potting size is between 10 and 14 months.

Color references are made to The Royal Horticultural Society Colour Chart (R.H.S.), 2007 edition, except where general colors of ordinary significance are used. Color values were taken under daylight conditions at approximately noon in Zaandammerweg, Assendelft, The Netherlands. The age of the 'Penny Love' plants described is 12 months after potting.

Classification:

*Botanical.*—*Phalaenopsis hybrida.*

Parentage:

*Female or seed parent.*—*Phalaenopsis* cultivar designated 'Sunrise Delight', unpatented.

*Male or pollen parent.*—*Phalaenopsis* cultivar designated 'Timothy Christopher', unpatented.

Propagation:

*Type.*—Tissue culture.

*Rooting habit and description.*—Fleshy; approximately 3 mm-6 mm wide and greyed/green in color (RHS 190B); freely branching. It takes 12 weeks for plants growing in tissue culture to initiate roots.

Plant:

*Size at maturity.*—Height (from bottom of pot to highest flower): about 38 cm. Spread: about 40 cm.

*Growth habit.*—Small; green leaves (RHS N137A) and a relatively normal raceme.

*Vigor.*—Moderate.

*Crop time.*—Following asexual propagation, at about 26 weeks 2 leaves appear; at about 30 weeks 3-4 leaves appear; after a cold treatment of about 4-8 weeks at a temperature of about 19° C. about 2 racemes with flowers appear.

Foliage:

*Quantity per plant.*—About 6-8 leaves are produced before flowering.

*Arrangement and attachment.*—Alternate, clasping.

*Overall shape of leaf.*—Oval; the tip is blunt and asymmetric.

*Texture (upper & underside).*—Smooth and leathery.

*Pubescence.*—None.

*Mature leaf length.*—About 17 cm.

*Mature leaf width.*—About 7 cm.

*Mature leaf thickness.*—About 2 mm.

*Mature leaf color.*—Upper side: green (RHS 137A). Under side: green (RHS 137A and RHS 137B).

*Leaf base.*—Acute.

*Margin.*—Entire.

*Venation.*—Pattern: parallel. Color of midvein: upper side: green (RHS 137A). under side: green (RHS 137C).

Inflorescence description:

*Appearance.*—Upright to slightly pendant, racemose inflorescence with bilaterally symmetrical flowers that open in succession beginning with the lowermost flower.

Raceme:

*Quantity per plant*.—About 1-4.

*Number of flowers per raceme*.—About 6-20.

*Length*.—About 18 cm.

*Diameter*.—About 30 cm.

Peduncle:

*Length*.—About 14 cm.

*Diameter*.—About 3 mm.

*Strength*.—Strong.

*Aspect*.—Upright.

*Texture*.—Glabrous and smooth.

*Color*.—Green (RHS 137B) with brown (RHS 200A).

Buds:

*Height* (*from base to tip*).—About 18 mm.

*Diameter* (*at midpoint*).—About 16 mm.

*Shape*.—Asymmetric oval.

*Color*.—Yellow/green (RHS 144D) and red/purple (RHS 71A).

*Orientation*.—Same as flowers (forward facing).

Flowering time: For an untreated plant (flowering plant that has not undergone cold-treatment where the plant grows at a temperature of 18° C. to 19° C. for about 4 to 8 weeks after a period of about 30 weeks at a temperature of 25° C.), 1-4 racemes appear with flower buds and flowers. First flowers can be expected approximately 4 to 6 months after planting a plant with a leaf diameter of 3 to 5 cm. Flowers persistent.

Flowering longevity: On the plant: about 4 to 6 months; lastingness of cut flowers: has not been observed.

Fragrance: No fragrance.

Flower:

*Rate of opening*.—Flowers fully opened about 2 to 3 days after petal and sepal separation.

*Orientation at opening*.—Slanted upward and outward.

Figure 2:
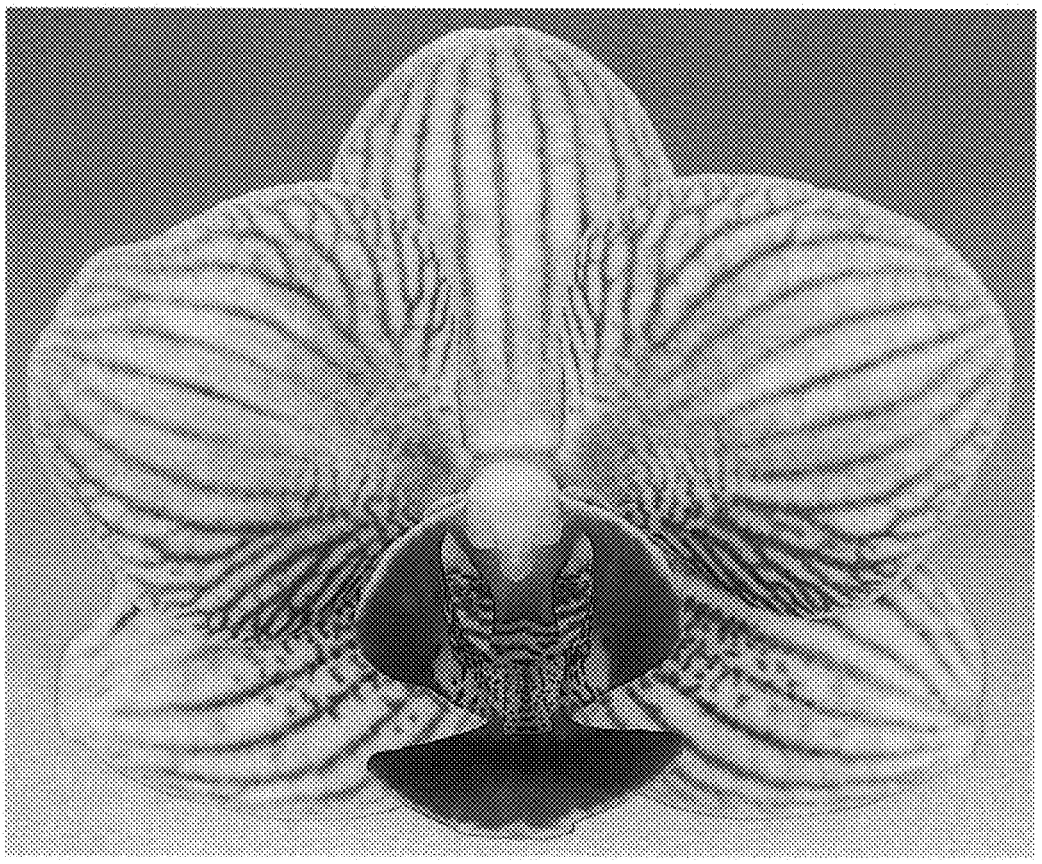
FIG. 2 shows a close-up view of the typical flower of 'Penny Love'.
Figure 3:
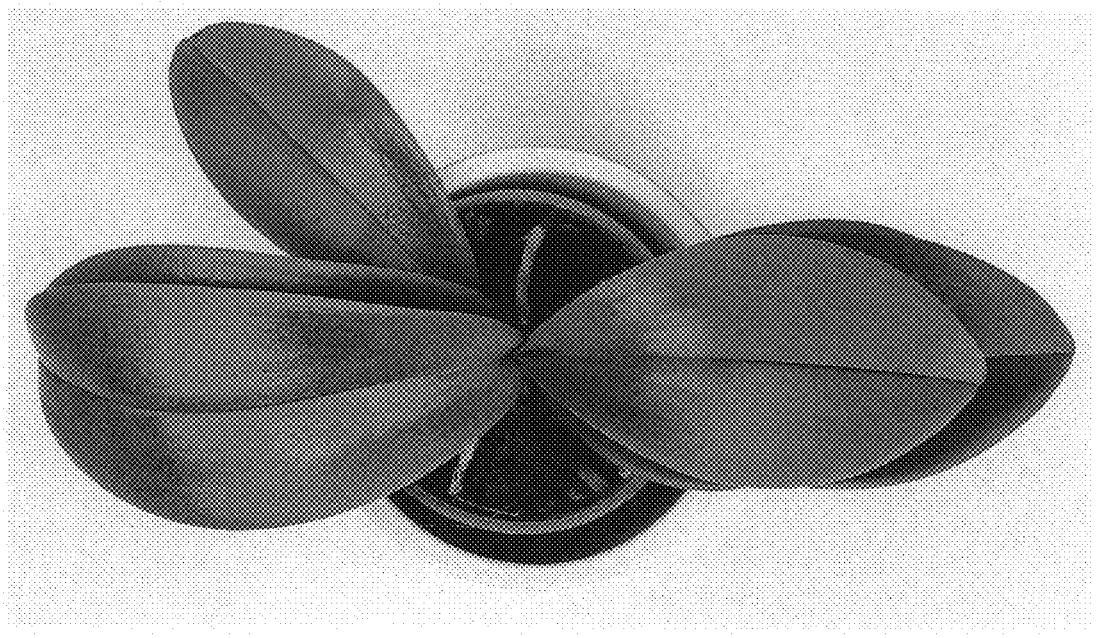
FIG. 3 shows a close-up view of the typical leaves of 'Penny Love'.

*Shape*.—Typical shape of *Phalaenopsis*; see FIG. 2.

*Size* (*of single bloom*).—Height: about 45 mm. Diameter: about 55 mm.

*Quantity and arrangement*.—Three petals and three sepals. Arrangement of petals are free, not touching. Petals are more pronounced than sepals.

Petals:

*Arrangement*.—Inner whorl comprises 3 petals: 2 lateral petals and a labellum.

2 *Lateral petals*.—Overall shape: broadly ovate and weakly cupped. Apex: round. Margin: entire and weakly undulate. Base: broadly ovate. Length: about 23 mm. Width: about 22 mm. Texture: Upper surface: smooth and satiny. Under surface: smooth and satiny. Color (when fully opened): upper side: yellow (RHS 8B and RHS 8C) with many red/purple (RHS 71A) stripes and a red/purple blush (RHS N78D) towards the base with a bit of white (RHS NN155C) at the base. There is also a few red/purple netting (RHS 71A) along the sides of the margin upper surface. Under side: yellow/green (RHS 154C) with red/purple stripes (RHS 71A). Labellum: Overall shape: 3-lobed with 2 prominent callosities at central junction of the lateral lobes and base of the midlobe. Lateral lobes of labellum fold upward about the column; the midlobe extends forward and is terminated by 2 stubs appendages at the apex. Lateral lobes of the labellum are ovate in shape while the midlobe is triangular with a bump and a rib on it. Margin of the midlobe and lateral lobes: entire and weakly undulate. Apex of the midlobe and lateral lobes: rounded. Length midlobe: about 17 mm. Width midlobe (not flattened): about 15 mm. Length lateral lobe: about 15 mm. Width lateral lobe (not flattened): about 7 mm. Depth of tube created by lateral lobes of labellum: about 7 mm. Texture of the midlobe and lateral lobes: Upper & under surface: smooth and satiny. Color (when fully opened): Midlobe, upper side: main color is red/purple (RHS N71A) with at the base some yellow (RHS 8B and RHS 8C) and at the end some purple (RHS N78A). There are not stripes and spots. Under side: at the base and in the edges red/purple (RHS 71A). In the center white (RHS NN155D). Lateral lobes, upper side: at the base some white (RHS NN155D) with yellow (RHS 8B and RHS 8C) and some red/purple spots (RHS 71A). Lower edge red/purple (RHS 71A) which runs into purple (RHS N78A). Under side: white (RHS NN155D) with some yellow (RHS 8A) at the base and upper edge. Rest is red/purple (RHS 71A) with purple (RHS N78A). Cirrhi: about 0.5 mm. color: yellow (RHS 8A). Pestle (Callosities): Length: about 3 mm. Width (not flattened): about 4 mm. Color: yellow (RHS 9A) with red/purple stripes/spots (RHS 71A).

Sepals:

*Arrangement*.—Outer whorl comprises 3 sepals, one dorsal and two lateral sepals.

*Overall shape*.—Elliptical and weakly cupped.

*Margin*.—Entire and weakly undulate.

*Length*.—About 21 mm.

*Width*.—About 18 mm.

*Apex*.—Rounded.

*Texture*.—Upper and under surface: smooth and satiny.

*Color* (*when fully opened*).—Upper side, dorsal: from the base white (RHS NN155D) with a red/purple blush (RHS N78D) which runs into yellow (RHS 8B and RHS 8C) with many red/purple stripes (RHS 71A) and a haze of yellow/green (RHS 154D). Lateral: at the base some white (RHS NN155D) which runs into yellow (RHS 8B and RHS 8C) with a moderate amount of red/purple spots and many stripes (RHS 71A) and a haze of yellow/green (RHS 154D). Under side, dorsal: yellow/green (RHS 154C and 154D) with some red/purple stripes (RHS 71A). Lateral: yellow/green (RHS 154C and 154D) with some red/purple stripes (RHS 71A).

Pedicel:

*Length*.—About 3,5 mm.

*Diameter*.—About 2 mm.

*Texture*.—Glabrous and smooth.

*Color*.—Yellow/green (RHS 154D) which runs into yellow/green (RHS 146C).

Reproductive organs:

Arrangement: The stamens, style and stigmas are fused into a single, short structure called the column, possessing one terminal anther with pollen grains united into a pollinia, which are covered by an anther cap. The stigma is located under the column behind the pollinia. The ovary is inferior with three carpels present. The plant has not produced seed.

Column:

*Length*.—About 1.8 mm.

*Diameter*.—About 3.5 mm.

*Color*.—Purple (RHS 78B) with yellow (RHS 8D).

Pollinia:

*Quantity*.—Two.

*Diameter*.—About 2 mm.

*Color*.—Yellow/orange (RHS 23A).

Ovary:

*Length*.—About 35 mm.

*Diameter*.—About 30 mm.

*Color*.—White (RHS NN155D).

Disease/pest resistance/susceptibility: No specific resistance or susceptibility observed.

Temperature tolerance: Tolerant to a low temperature of about 15° C. and to a high temperature about 30° C.

What is claimed is:

1. A new and distinct *Phalaenopsis* plant named 'Penny Love', as illustrated and described herein.

* * * * *